United States Patent [19]

Rohrbach et al.

[11] Patent Number: 4,865,976
[45] Date of Patent: Sep. 12, 1989

[54] METHOD OF CYCLODEXTRIN MANUFACTURE USING AN IMMOBILIZED CYCLODEXTRIN GLYCOSYLTRANSFERASE

[75] Inventors: Ronald P. Rohrbach, Forest Lake; Dale S. Scherl, Mt. Prospect, both of Ill.

[73] Assignee: UOP, Des Plaines, Ill.

[21] Appl. No.: 905,599

[22] Filed: Sep. 10, 1986

[51] Int. Cl.$^4$ .................... C12P 19/18; C12P 19/08
[52] U.S. Cl. ................................. 435/103; 435/97; 435/178
[58] Field of Search ............... 435/97, 193, 178, 188, 435/803, 813, 103, 859

[56] References Cited

U.S. PATENT DOCUMENTS

| | | | |
|---|---|---|---|
| 3,923,598 | 12/1975 | Horikoshi | 195/31 R |
| 4,141,857 | 2/1979 | Levy et al. | 252/430 |
| 4,317,881 | 3/1982 | Yagi et al. | 435/193 |
| 4,477,568 | 10/1984 | Hoske et al. | 435/803 |
| 4,593,004 | 6/1986 | Boross et al. | 435/181 |

OTHER PUBLICATIONS

J. Szejtli, *Starch*, 34, 379–85, (1982).
K. Horikoshi, *Process Biochemistry*, May 1979 (26–30).
M. Matzuzawa et al., *Die Starke*, 27, 410–13, (1975).

*Primary Examiner*—Barry S. Richman
*Assistant Examiner*—T. J. Wallen
*Attorney, Agent, or Firm*—Thomas K. McBride; Eugene I. Snyder

[57] ABSTRACT

A process for the continuous production of cyclodextrins employs as a feedstock an aqueous solution of partially hydrolyzed starch with a dextrose equivalent between about 10 and about 15 as the feedstock for an immobilized cyclodextrin glycosyltransferase. In one variant the feedstock is sent to a membrane which removes cyclodextrins and glucose and the retentate is recycled to an immobilized glycosyltransferase so as to effectively utilize the feedstock. In another variant the effluent is passed through a water immiscibled liquid organic compound which forms a solid insoluble complex with cyclodextrins, the solids are continually removed, and the aqueous phase is recycled to an immobilized cyclodextrin glycosyltransferase as in the prior variant.

16 Claims, 3 Drawing Sheets

CYCLODEXTRIN FORMATION WITH MEMBRANE SEPARATION

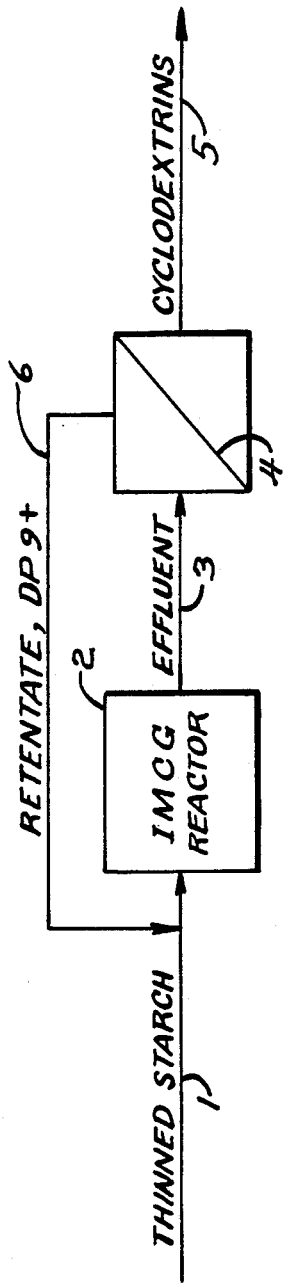
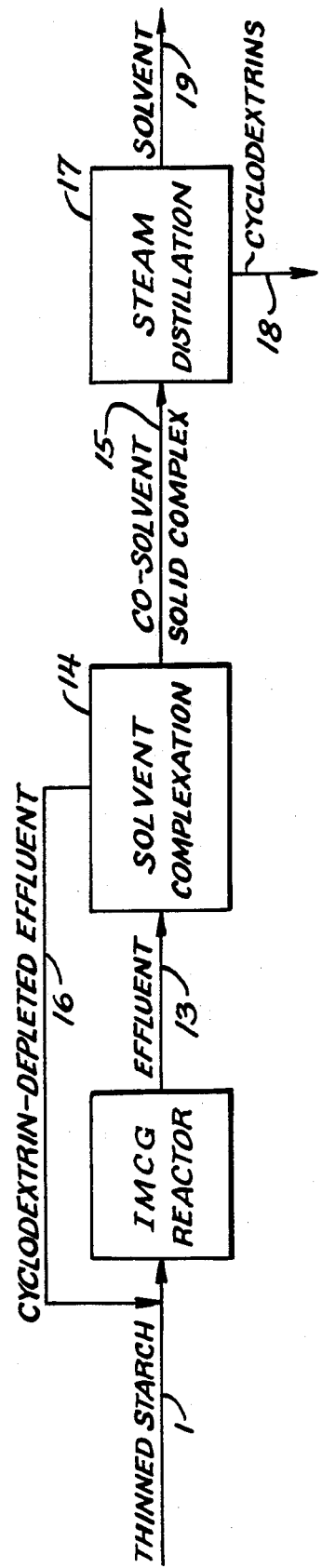

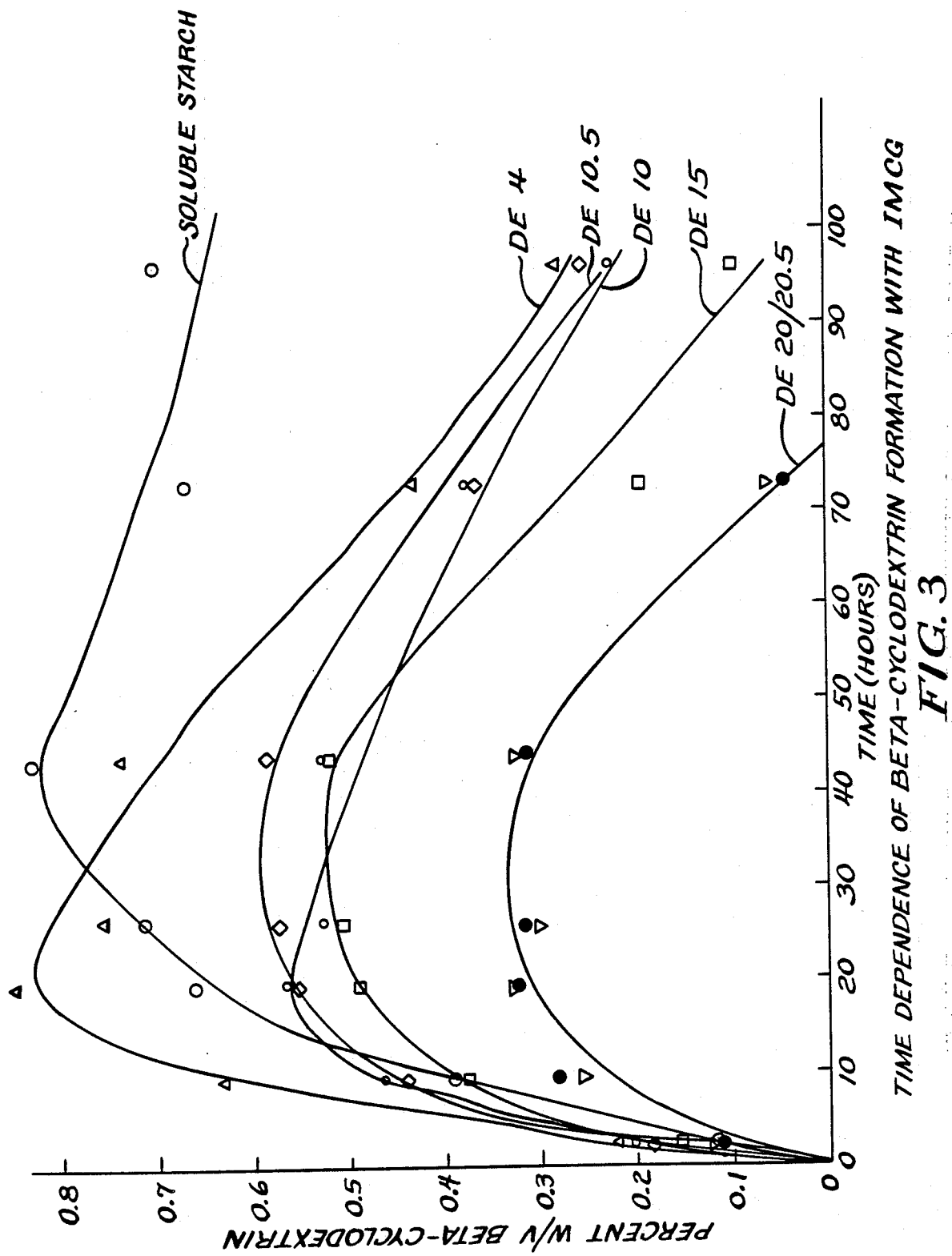

TIME DEPENDENCE OF BETA-CYCLODEXTRIN
FORMATION WITH SOLUBLE CG

METHOD OF CYCLODEXTRIN MANUFACTURE USING AN IMMOBILIZED CYCLODEXTRIN GLYCOSYLTRANSFERASE

BACKGROUND OF THE INVENTION

Cyclodextrins are cyclic molecules consisting of 1-4 linked alpha-D-glucopyranose monomeric units. The cyclodextrins containing 6-, 7-, and 8-membered rings, commonly known as alpha-, beta-, and gamma-cyclodextrin, respectively, are the most important cyclodextrins to date, possibly because of their availability relative to cyclodextrins of different ring size. The usefulness of these cyclodextrins arises from their ability to reversibly form inclusion complexes, or clathrates, with many types of compounds. Inclusion complexes arise when a host molecule, such as cyclodextrin, has a structure containing an interior cavity into which guest molecules can bind by weak interactions such as van der Waal's forces. The latter are short range forces which are sufficiently strong to allow the formation of definite, generally solid complexes, but are sufficiently weak to permit ready dissociation of the complex to a host and guest molecule.

The cyclodextrins are doughnut-shaped molecules with an interior cavity whose size and shape is determined by the number of glucose units that make up the ring. In alpha-cyclodextrin the almost cylindrical cavity is approximately 7 angstroms deep and 5 angstroms in diameter. In beta-cyclodextrin the depth is the same but the diameter is 7 angstroms, and in gamma-cyclodextrin it is again 7 angstroms deep but 9 angstroms in diameter. Cyclodextrins are soluble in water because of the many hydroxyl groups of the glucose subunits that surround the rim of the cavity. However, the interior of the cavities themselves are hydrophobic, and these hydrophobic cavities extract organic molecules from aqueous solution if the organic materials have the correct shape and hydrophobic character.

The complexing ability of cyclodextrins lends itself to various uses. For example, the cyclodextrins are used in encapsulating desirable flavors and fragrances which can then be stored for reasonably long periods of time and added to foods at their preparation. Reciprocally, cyclodextrins may be used in removing undesirable flavors and fragrances from food by complexing with them. Cyclodextrins also are used in the protection of foods against oxidation, photochemical degradation, and thermal decomposition. These and other uses have been summarized by J. Szejtli, *Starch*, 34, 379–385 (1982)

To date cyclodextrins have been prepared by treating starch with a cyclodextrin glycosyltransferase (CG) first at a high temperature to liquefy the starch, then at a lower temperature to form the cyclodextrins from the liquefied starch. Although many variations are possible all utilize a liquid starch of low dextrose equivalent (DE), less than about 4, as a substrate for the enzyme. The prior art methods have been described and summarized by K. Horikoshi, *Process Biochemistry*, May, 1979, 26–30, and by M. Matzuzawa et al., *Die Starke*, 27, 410–413 (1975).

For continuous production of cyclodextrins as well as for minimizing enzyme cost and maximizing enzyme utilization a process using a cyclodextrin glycosyltransferase immobilized as a fixed or fluidized bed would be advantageous. In such a process the use of liquefied starch as a feed is an undesirable limitation, because the low starch solubility, on the order of 1% w/v, limits both cyclodextrin productivity (the amount of cyclodextrin formed per unit time) and cyclodextrin concentration in the product mixture. A high cyclodextrin concentration in the product mixture is desirable to facilitate subsequent cyclodextrin purification. Although a suspension of liquefied potato starch has been used as a feedstock for soluble CG, it is an unacceptable feedstock for a bed of immobilized cyclodextrin glycosyltransferase (IMCG) which would effectively behave as a filtering aid to remove the suspended particles, ultimately leading to bed plugging.

With the above in mind it was thought that use of thinned starch, that is, a partially hydrolyzed starch, as the feedstock for IMCG might be beneficial. Initial experiments quickly demonstrated different limitations characteristic of this new feed. Thus, cyclodextrin conversion decreases with increasing dextrose equivalent and increasing dry solids content. This results from enzyme inhibition by glucose initially present in the partially hydrolyzed starch and which also is formed by various disproportionation reactions effected by CG itself. It was also observed that cyclodextrin formation passes through a maximum which arises from a slow hydrolysis of cyclodextrin catalyzed by CG, a reaction which produces glucose further inhibiting cyclodextrin formation by the enzyme.

Our results suggested that a process using partially hydrolyzed starch as a feed for IMCG required maximizing the dry solids to maximize the cyclodextrin concentration in the product mix and cyclodextrin productivity, but at the same time minimizing glucose formation, or at least minimizing the effects of glucose inhibition on CG activity. Because the conversion of partially hydrolyzed starch to cyclodextrins is substantially lower than that with liquefied starch, any process utilizing partially hydrolyzed starch as the feedstock for IMCG needs to provide a means of reusing the oligosaccharides in the product mixture as a feed for IMCG so as to provide for the efficient and economical utilization of thinned starch as a feedstock, but without any detrimental effects on cyclodextrin formation.

Our solution to the two aforementioned problems leads to processes for the efficient, economical, and continuous production of cyclodextrins from thinned starch using immobilized cyclodextrin glycosyltransferase. In particular, the process of our invention separates glucose and/or cyclodextrins from the effluent of an IMCG reactor and recycles the oligosaccharide-rich stream to the IMCG reactor. Where only cyclodextrins are separated they are formed under conditions where glucose formation, and consequent enzyme inhibition, is minimized.

One advantage of the processes which are our invention is the efficient use of enzymes. Because the CG is effectively reused, the enzyme cost is substantially reduced. Another advantage is to afford a method of producing cyclodextrins in a continuous process. Still another advantage is that the relative proportion of the components in the mixture of cyclodextrins that is formed may be controlled somewhat by changing the reaction conditions. Yet another advantage is that the processes described herein afford good quality control over the cyclodextrins produced. Our processes afford high purity beta-cyclodextrin in good yield from a readily available and relatively inexpensive feedstock, all of which are highly advantageous.

SUMMARY OF THE INVENTION

An object of this invention is to prepare cyclodextrins in a continuous process using an immobilized cyclodextrin glycosyltransferase acting on a feedstock of thinned starch. An embodiment is a process where the feedstock to an IMCG reactor has a dextrose equivalent between about 10 and about 15, the effluent from the reactor is used as the feedstock for a membrane passing glucose and cyclodextrin, with the retentate being recycled to the IMCG reactor. In a more specific embodiment the dry solids content of the feedstock is between about 0.2 and about 30 weight-volume percent. In another embodiment the effluent from the IMCG reactor is passed into a water-immiscible liquid organic compound which forms a solid, insoluble complex with one or more of the cyclodextrins in the product mixture and the cyclodextrin-depleted aqueous phase is recycled to the IMCG reactor. In a more specific embodiment the reaction is conducted at a pH between about 5.5 and about 7.5. Other embodiments will be apparent from the ensuing description.

DESCRIPTION OF THE FIGURES

FIG. 1 shows a flow diagram for continuous production of cyclodextrin with product separation by a semipermeable membrane.

FIG. 2 shows a flow diagram for continuous production of cyclodextrin with product separation by formation of an insoluble complex.

FIGS. 3 and 4 show the time dependence of beta-cyclodextrin formation with IMCG and soluble enzyme, respectively, as a function of feedstock D.E.

DESCRIPTION OF THE INVENTION

Figure 4:
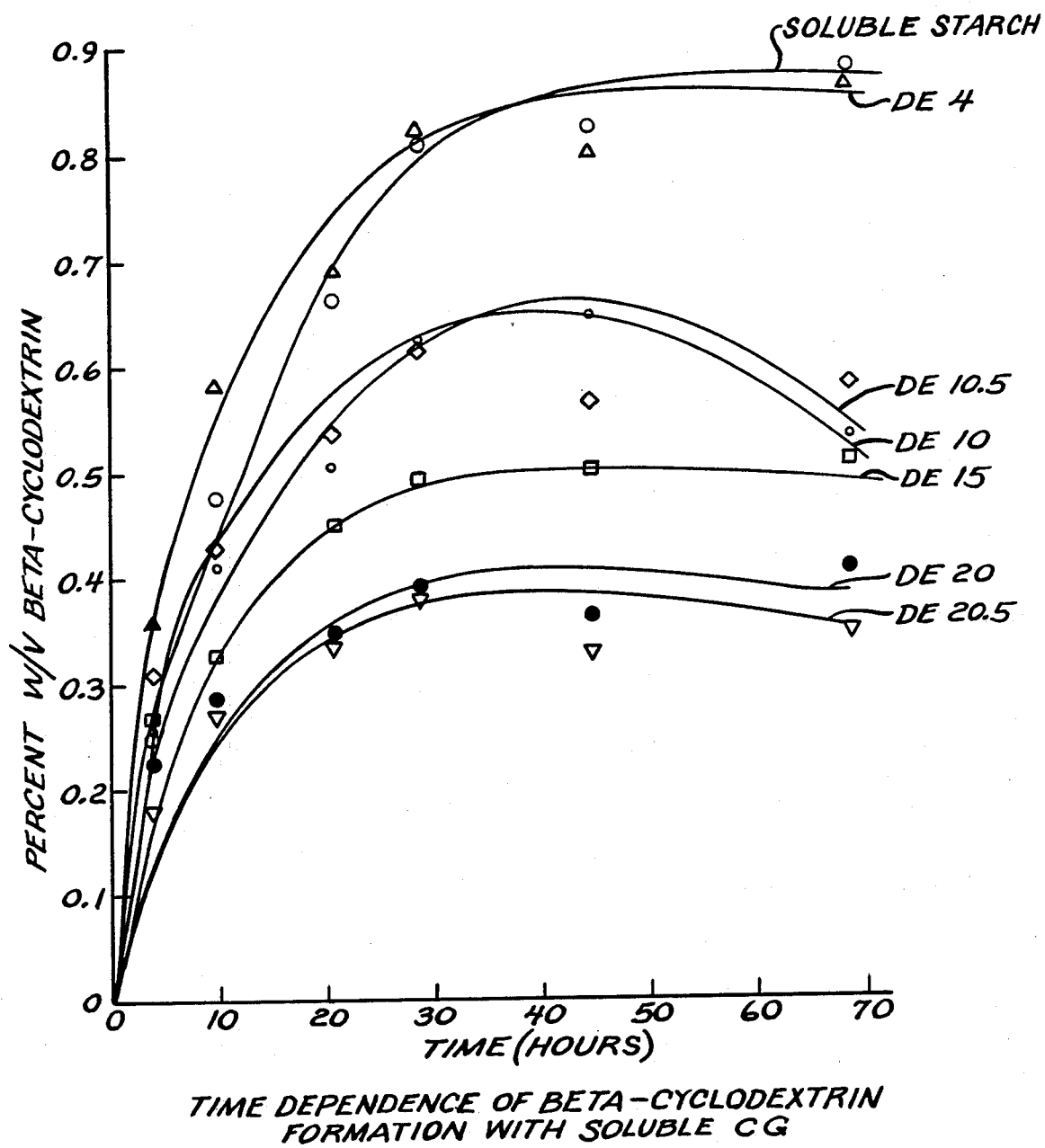

This application is directed toward a method of making cyclodextrins by reacting an aqueous feedstock of partially hydrolyzed starch with an immobilized cyclodextrin glycosyltransferase. In one variant the effluent from the IMCG reactor is passed over a membrane which freely passes cyclodextrins and glucose, the permeate is collected, and the retentate is returned to an IMCG reactor. In another variant the effluent is passed into a water-immiscible liquid organic compound which forms an insoluble complex with at least one of the cyclodextrins in the effluent, the insoluble solids are collected and treated to release the cyclodextrins which are then recovered, and the aqueous phase in contact with the immiscible liquid organic compound is then recycled to the IMCG.

The feedstocks which are used in the practice of this invention are partially hydrolyzed starch, commonly known as thinned starch, with a dextrose equivalent (DE) between about 10 and about 15. Although partially hydrolyzed starch with a DE as low as about 5 and as high as about 25 may be used in the practice of this invention, it has been found that a DE between about 10 and 15 affords the best results, in part because higher DE feedstocks manifest severe glucose inhibition of enzymatic activity. The feedstocks typically have a dry solids (DS) content in the range between about 0.2 and about 30 weight-volume percent, although the range between about 1 and about 10% w/v affords the best compromise in the practice of this invention.

A feedstock of an aqueous solution of partially hydrolyzed starch is then reacted with an immobilized cyclodextrin glycosyltransferase to convert the oligosaccharides in the feedstock to a mixture of cyclodextrins.

The immobilized cyclodextrin glycosyltransferase as used in this application is a generic one, that is, neither the nature of the enzyme nor the nature of the support system used in making the immobilized enzyme is critical to the success of this invention, although it is not implied that all IMCG's are equivalent in the practice of this invention. Suitable sources of the enzyme have been reported by Horikoshi, op, cit., but that from the Bacillus sp. ATCC 2173 (U.S. Pat. No. 3,923,598) have been most often used in obtaining the results reported in this application. Similarly, any support matrix may be used to immobilize the CG, some recent examples of which appear in U.S. Pat. No. 4,593,004. However, we have preferred to use the support matrix of Levy and Fusee as described in U.S. Pat. No. 4,141,857 to prepare our IMCG. The support matrix is essentially a refractory inorganic oxide which is impregnated with a polyamine subsequently cross-linked by an excess of a bifunctional reagent so as to afford pendant functional groups. Among the oxides which may be used are included alumina, silica, titania, thoria, magnesia, and combinations thereof, with alumina being employed most often. The polyamines include diethylenetriamine, triethylenetetraamine, tetraethylenepentamine, pentaethylenehexamine, and polyethyleneimine, especially of a molecular weight between about 1200 and 100,000. The bifunctional reagents which are used include phthalaldehyde, toluenediisocyanate, and compounds of the formula $X(CH_2)_pX$, where p is an integer from 2 to 8, and X is —NCO or —CHO. A support matrix where the polyamine is polyethyleneimine cross-linked by an excess of glutaraldehyde (X= —CHO and p=5) on alumina has been the support matrix most commonly employed by us in the preparation of an IMCG. However, it needs to be again emphasized that the success of this invention is not dependent upon the use of any particular IMCG, even though not all may give equivalent results.

The feedstock of an aqueous solution of partially hydrolyzed starch is then reacted with the immobilized cyclodextrin glycosyltransferase, generally in a fixed bed, although an ebullated or fluidized bed also may be employed, at a temperature between about 45° and about 70° C., even more commonly between about 50° to about 60° C. It has been found that the IMCG used by us has a half life at 50° C. well in excess of 150 days, which is far greater than the half life of the soluble enzyme under comparable reaction conditions.

The pH under which the reaction is conducted affords a secondary means of control which allows some degree of latitude in the composition of the effluent. The pH exerts a effect both on the extent of conversion of oligosaccharides to cyclodextrins as well as the distribution of alpha-, beta-, and gamma-cyclodextrins formed. Thus, it has been found that total cyclodextrin formation is maximized at a pH of about 7, but that formation of gamma-cyclodextrin is reduced to a value near 0 at a pH in the range of 6.0–6.5. Consequently, if total cyclodextrin yield is of greater importance then the reaction is best performed at a pH of 7.0, but where product purity of beta-cyclodextrin is of greater importance then it is advantageous to conduct the reaction at a lower pH so as to minimize formation of gamma-cyclodextrin and facilitate purification of the beta-cyclodextrin from a much simpler product mixture.

The effluent from the IMCG reactor is the product mixture and in one variant of our invention, which is the preferred embodiment, it may be sent to a membrane, and in another variant of our invention it may be mixed with a water-immiscible liquid organic compound, hereafter sometimes referred to as a complexing agent, which forms an insoluble complex with at least one of the cyclodextrins. These two variants are discussed separately below.

Where the effluent is sent to a membrane, the membrane employed is one that freely passes cyclodextrin and glucose while retaining oligosaccharides higher than about DP9. The purpose of the membrane separation is to remove at least most of the cyclodextrin and virtually all of the glucose from the effluent. As previously mentioned, glucose is an inhibitor for the enzymatic action of CG. Therefore, if the unreacted oligosaccharides in the effluent are to be reused in cyclodextrin production it is at least desirable, if not necessary, to remove as much glucose as possible. It also is desirable to remove as much cyclodextrins as possible, not only because these are the desired products but also because cyclodextrins are hydrolyzed by the transferase.

It has been found that an ultrafiltration membrane, especially one with a molecular weight cutoff from about 2000 to about 5000 is very successful in performing the aforementioned separation. The permeate is collected and the cyclodextrins contained therein are then separately recovered. The retentate from the membrane separation is then used as a feedstock for a IMCG reactor. This could be a reactor in series, or a separate reactor, but it is preferred that the retentate be recycled to the reactor affording the effluent which is the membrane feed.

In another variant of our invention the effluent is passed into a water-immiscible liquid organic compound which forms an insoluble complex with at least one of the cyclodextrins in the effluent. Generally the beta-cyclodextrin is the predominant one in the cyclodextrin product mixture, and therefore it is preferred to use a complexing agent which efficiently forms an insoluble complex with beta-cyclodextrin. Among the complexing agents which may be effectively used in the successful practice of this invention are included chloroform, methylene dichloride, the hexanes, carbon tetrachloride, toluene, ethylcyclohexane, trans-1,2-dimethyl cyclohexane, methylcyclohexane, cyclohexane, cyclohexene, tetralin, isooctane, ortho-xylene, para-xylene, meta-xylene, and decalin. Among those liquid organic compounds which are particularly suitable are included toluene, ortho-xylene, trans-1,2-dimethyl cyclohexane, and tetralin, for all of these form insoluble complexes whose solubility constant is sufficiently low as to insure removal of virtually all beta-cyclodextrin from the effluent.

The aqueous phase is then reused as a feedstock for further reaction with an IMCG. As in the prior variant, such an IMCG may be another reactor in series, another reactor completely independent of the one used in its production, or in the preferred mode the aqueous phase may be recycled to the IMCG at the front end of the process train.

The solid insoluble complex of cyclodextrin with an liquid organic compound is then collected by any suitable means, as for example by centrifugation or by filtration. This solid is then treated to release cyclodextrin from the complex. Most often this is done by merely steam treating the solid complex, i.e., the solid complex is mixed with a small amount of water, the mixture is heated so as to dissociate the complex into its component cyclodextrins and complexing agent, and the complexing agent is removed along with at least some of the water as a vapor. However other methods may be employed to release the liquid organic compound from the solid complex cyclodextrin, and these methods include merely heating the complex with water so as to effect dissociation and dissolve the released cyclodextrin, and separating the organic phase from this hot mixture and recovering the cyclodextrins from the cooled aqueous phase. Other methods of releasing the cyclodextrins from the insoluble solid complex also may be used, such as heating the complex with an aqueous solution of a second complexing agent to displace the first one so as to form a soluble complex, and changing the pH so as to alter the charge on the included complexing agent thereby rendering the binding force so weak as to dissociate the complex.

Our invention may be more readily understood with reference to the flow diagrams of FIGS. 1 and 2. In FIG. 1 the feedstock, 1, of partially hydrolyzed starch of a D.E. between about 10 and 15 with a dry solids content between about 1–10% w/v and a pH of between about 5 and about 9 is passed into a reactor, 2, containing a bed of IMCG. Most normally a fixed bed is used, although an ebullated bed or fluidized bed also may be used in the practice of this invention. The effluent, 3, from the reactor contains cyclodextrins in an amount which depends upon, inter alia, upon the nature of the feedstock, the pH in the reactor, and the temperature at which reaction is conducted. This effluent is then passed over a membrane, 4, with the permeate 5, containing largely cyclodextrins and glucose. It also may be noted that the permeate can contain oligosaccharides such as DP2, DP3, up to about DP8. The retentate 6, contains largely higher oligosaccharides, mainly DP9 and above. In the preferred practice of our invention this retention is recycled to the IMCG reactor where it is blended with the incoming feedstock 1.

FIG. 2 shows a second variant whose initial portion is analogous to the previously described flow diagram. Thus, feedstock 1 is passed to an IMCG reactor operating at appropriate reaction conditions of temperature and pH to afford an effluent 13 which is the product cyclodextrin stream. This product stream is mixed with a water-immiscible liquid organic compound so as to form an insoluble complex of at least one of the cyclodextrins in the reactor 14. The cyclodextrin-depleted aqueous phase, 16, is then recycled to the reactor 12. The insoluble solid complex, 15, is removed from the reactor 14 and passed into the steam distillation unit, 17, whereby liquid organic compound, 19, is removed by steam distillation along with copies quantities of water. A concentrated aqueous solution of cyclodextrin is removed as the stream 18, and the cyclodextrins are recovered therefrom, generally by crystallization.

In a particularly advantageous operational embodiment of the process as depicted in FIG. 2 there is utilized a biphasic reactor consisting of a fluidized bed of IMCG with a head of water-immiscible liquid organic compound which forms a complex with at least one of the formed cyclodextrins. The aqueous feedstock is passed up through the fluidized bed and when it comes in contact with the water-immiscible liquid organic compound there is formed an insoluble, solid complex of solvent with at least one of the cyclodextrins. This solid falls to the bottom of the reactor, where it is removed and collected, and the aqueous phase is then recycled. A small bleed of the aqueous phase insures a manageable and feasible concentration of oligosaccharides in the feedstock at all times.

The following examples are merely illustrative of our invention and are not to be limited thereto.

EXAMPLE 1

Effect of substrate DE on cyclodextrin formation. Feedstocks of 2.0% w/v solutions of soluble starch and of thinned starch of dextrose equivalent between 4.0 and about 20.5 were prepared using 5 mM glycine at pH 9.0. A mixture of 10.0 mL of each feedstock and 0.10 g of an immobilized glycosyltransferase (approximately 500,000 units/gram) were reacted with shaking at 40° C. Samples were removed (1.0 mL) and analyzed for alpha-, beta-, and gamma-cyclodextrins at various times. A plot of beta-cyclodextrin concentration versus time is shown in FIG. 3. A similar set of experiments was performed using soluble enzyme and these results are graphically displayed in FIG. 4.

What FIG. 3 demonstrates is that the maximum amount of betacyclodextrin formed (as well as the total amount of cyclodextrins formed) varies with the extent of hydrolysis of the feedstock. Thus, the lower the DE of the feedstock the greater is the maximum cyclodextrin formation. The figure also shows that the maximum amount of beta-cyclodextrin formed is about the same for soluble starch as it is for a thinned starch of DE 4. The figure also clearly shows that beta-cyclodextrin concentration first increases, goes through a maximum, and thereafter decreases. This results from the subsequent hydrolysis of beta-cyclodextrin by glycosyltransferase. Finally, the figures also show that the maximum beta-cyclodextrin concentration is reached at different times depending upon the substrate. It is particularly noteworthy that although the maximum concentration for both soluble starch and a thinned starch of DE 4 is about the same, the time at which it is reached is about half for the thinned starch substrate. FIG. 4 shows somewhat similar behavior for the soluble enzyme, although there appears to be a less pronounced maximum than is the case with the immobilized enzyme.

EXAMPLE 2

Variation of cyclodextrin conversion with dry solids content. To 1 gram of alumina (ca. 60–80 mesh) was added polyethyleneimine as a 1.8% w/v aqueous (10 ml solution per gram alumina). The mixture was degassed, and after being contacted for 3–4 hours solid was removed by filtration and air dried. To the dried solid was added 10 ml of a 5% w/v aqueous solution of glutaraldehyde. After one hour at room temperature solid again was collected by filtration and thoroughly washed with water to remove any residual glutaraldehyde. To this activated support was added 250,000–500,000 units of glycosyltransferase (50–100 mg protein per gram of support). Reaction was continued for 16 hours at 4° C., after which excess enzyme was removed and the support thoroughly washed with water. The IMCG then was loaded into a thermostated column.

Enzyme activity was determined by a KI assay using as a substrate 0.3 ml of a 0.2% soluble starch solution containing 5 mM phosphate buffer at pH 9.0 and 5 mM $CaCl_2$. To this was added 10 lambda of the enzyme solution to be assayed and the mixture was incubated for 10 minutes at 40° C. The assay mixture was quenched with 4 ml of 0.2N HCl, after which 0.5 ml of a solution containing 0.02% $I_2$ and 0.2% KI was added. The optical density was determined at 700 nm and compared with a blank (no enzyme added). One unit of activity is defined as that necessary to result in a 1% change in optical density.

An aqueous solution of thinned starch of DE 15 containing 5 mM $CaCl_2$, 5 mM imidazole, and 100 ppm sodium omadine at pH 7.0 was prepared at various dry solids levels. At reactor was loaded with 1.0 cc of IMCG (0.31 g, ca. 500,000 units/g) and 200 ml of the substrate was batch recycled at 50° C. Samples were removed at different times and analyzed by high pressure liquid chromatography. The table below summarizes data for maximum conversion to beta-cyclodextrin, its concentration at maximum conversion, and the time to achieve maximum conversion.

TABLE 1

Variation of Conversion to Cyclodextrin with Dry Solids.

| Dry solids | % Conversion, maximum (beta) | % Concentration (w/v) at maximum (beta) | Time to maximum (hrs) |
|---|---|---|---|
| 2.0 | 20.8 | 0.416 | 24 |
| 5.0 | 13.6 | 0.679 | 42 |
| 9.9 | 8.0 | 0.792 | 52 |
| 18.5 | 4.1 | 0.785 | 60 |
| 29.0 | 2.7 | 0.783 | 95 |

EXAMPLE 3

Variation of IMCG activity with pH. Solutions of 0.2% w/v soluble starch were prepared at a different pH and used as a substrate for IMCG at 40° C. After 20 minutes enzyme activity was measured using the assay previously described. Results are tabulated in table 2.

TABLE 2 pH Dependence Of IMCG Activity

| pH | Activity Units/G |
|---|---|
| 4.0 | 411 |
| 5.0 | 527 |
| 6.1 | 459 |
| 7.0 | 379 |
| 8.0 | 342 |
| 9.0 | 231 |

EXAMPLE 4

Distribution of cyclodextrins with pH. Substrates of 2.0% soluble starch containing 5 mM $CaCl_2$ and 5 mM of a suitable buffer (acetate, imidazole, or glycine) were prepared. These solutions were used as the substrate for soluble starch, and the maximum concentration of beta-, and gamma-cyclodextrin as a function of pH is tabulated below.

TABLE 3

Cyclodextrins Variation with pH.

| pH | Beta-Cyclodextrin (mg/ml) | Gamma-Cyclodextrin (mg/ml) |
|---|---|---|
| 4.0 | 0.15 | — |
| 4.5 | 0.86 | — |
| 5.0 | 1.12 | — |
| 6.0 | 1.45 | — |
| 7.0 | 1.46 | 0.41 |
| 8.0 | 1.38 | 0.39 |
| 9.0 | 1.03 | 0.09 |
| 9.5 | 0.65 | 0.29 |

EXAMPLE 5

Cyclodextrin formation from thinned starch using IMCG with membrane separation. Thinned starch of DE 15 at 2% dry solids and containing 5 mM $CaCl_2$, 5 mM imidazole, and 100 ppm sodium omadine at pH 7.0 was reacted with an immobilized glycosyltransferase at 50° C. at a liquid hourly space velocity of 4.5. The effluent was passed over an ultrafiltration membrane (a polysulfone) with a molecular weight cutoff of about 5,000. The retentate, which contained oligosaccharides of DP9 and higher, was freeze dried and used to make a 2.0% w/v solution with the same additives as the original feedstock at pH 7.0 and used as the feedstock for another IMCG under similar operating conditions as described above. A control experiment using only thinned starch of DE 15 with the same reactor under comparable reaction conditions was performed. The retentate afforded 14.3% beta-cyclodextrin at maximum conversion, whereas the control afforded 24.7% beta-cyclodextrin. This demonstrates that at least 39% conversion to beta-cyclodextrin can be achieved by reusing the retentate from membrane separation as the feedstock for an IMCG.

EXAMPLE 6

Biphasic reaction with toluene as the water-immiscible phase. A reactor used 2.0 w/v% thinned starch of DE 15, pH 7.0, with the same additives as contained in the prior example. A biphasic reactor consisted of 3.5 cc (1.08 g) IMCG, 190 mL of feedstock, and 6.0 mL of toluene on a 25 mesh screen. The mixture was stirred at room temperature, and as the cyclodextrins were made they were precipitated by complexation with the toluene. A control was run omitting toluene. In the biphasic run the production of cyclodextrins could not be measured directly. Instead the production of cyclodextrins was directly related to the amount of dissolved solids left in solution. Hydrolysis of the samples causes all of the starch left in the solution to be converted to glucose whose concentration can be compared to the amount of glucose, in the hydrolyzed sample of the starting material. Percent conversion was calculated from the formula, $$\text{percent conversion} = \left[ \frac{G(i) - G(s)}{G(i)} \right] \cdot 100$$

wherein G(i) is the initial glucose concentration, and G(s) is the glucose concentration of the sample. In the control experiment since the cyclodextrins still were in solution the hydrolyzed samples could be analyzed by high pressure liquid chromatography. Results were that the maximum conversion to cyclodextrins for the control was 19.0%, whereas the maximum conversion in the biphasic reaction was 53.0%.

What is claimed is:

1. A method of making cyclodextrins comprising reacting at a temperature between about 45° and about 70° C. and at a pH from about 5.5 to about 7.5 an aqueous feedstock of partially hydrolyzed starch of a dextrose equivalent about 10 and about 15 and with a dry solids content from about 0.2 to about 30 weight-volume percent with an immobilized cyclodextrin glycosyltransferase to afford an effluent containing soluble cyclodextrins, passing the effluent over a membrane which freely passes cyclodextrins and glucose, collecting the cyclodextrin enriched permeate and further reacting the cyclodextrin and glucose depleted retentate with an immobilized cyclodextrin glycosyltransferase.

2. The method of claim 1 wherein the temperature is about 50° and about 60° C.

3. The method of claim 1 where the membrane is an ultrafiltration membrane.

4. The method of claim 3 where the membrane has a molecular weight cut-off between about 2000 and about 5000.

5. The method of claim 1 wherein the immobilized cyclodextrin glycosyltransferase results from immobilizing a cyclodextrin glycosyltransferase on a support matrix of a refractory inorganic oxide selected from the group consisting of alumina, silica, thoria, titania, magnesia, and combinations thereof impregnated with a polyamine selected from the group consisting of diethylenetriamine, triethylenetetramine, tetraethylenepentamine, pentaethylenehexamine, and polyethyleneimine cross-linked by an excess of a polyfunctional reagent selected from the group consisting of phthalaldehyde, toluene diisocyanate, and compounds of the formula $X(CH_2)_pX$, where p is an integer from 2 to about 8 and X is —NCO or —CHO, so as to afford pendant functional groups.

6. The method of claim 5 wherein the oxide is alumina, the polyamide is polyethyleneimine, and the bifunctional reagent is glutaraldehyde.

7. The method of claim 1 where the dry solids content is between about 1 and about 10 weight-volume percent.

8. A method of making cyclodextrins comprising reacting an aqueous feedstock of partially hydrolyzed starch of a dextrose equivalent between about 10 and about 15 and a dry solids content of about 0.2 to about 30 weight-volume percent with an immobilized cyclodextrin glycosyltransferase to afford an effluent stream containing soluble cyclodextrins, passing the effluent into a water-immiscible liquid organic compound which forms an insoluble solid complex with at least one of the cyclodextrins in the effluent, recycling the aqueous phase to the immobilized cyclodextrin glycosyltransferase, collecting the insoluble complex, releasing the complexed cyclodextrins by steam distillation, and recovering the cyclodextrins released thereby.

9. The method of claim 8 where the reaction is conducted at a temperature between about 45° and about 70° C.

10. The method of claim 9 where the temperature is between about 50° and about 60° C.

11. The method of claim 8 where the reaction is conducted at a pH between about 5.5 and about 7.5.

12. The method of claim 8 where the immobilized cyclodextrin glycosyltransferase results from immobilizing a cyclodextrin glycosyltransferase on a support matrix of a refractory inorganic oxide selected from the group consisting of alumina, silica, thoria, titania, magnesia, and combinations thereof impregnated with a polyamine selected from the group consisting of diethylenetriamine, triethylenetetramine, tetraethylenepentamine, pentaethylenehexamine, and polyethyleneimine cross-linked by an excess of a poly functional reagent selected from the group consisting of phthalaldehyde, toluene diisocyanate, and compounds of the formula $X(CH_2)_pX$, where p is an integer from 2 to about 8 and X is —NCO or —CHO so as to afford pendant functional groups.

13. The method of claim 12 where the oxide is alumina, the polyamine is polyethyleneimine, and the bifunctional reagent is glutaraldehyde.

14. The method of claim 8 where the liquid organic compound is selected from the group consisting of chloroform, methylene chloride, hexanes, carbon tetrachloride, toluene, ethyl cyclohexane, trans-1,2-dimethyl cyclohexane, methyl cyclohexane, cyclohexane, cyclohexene, tetralin, isooctane, the xylenes, and decalin.

15. The method of claim 14 where the solvent is toluene, tetralin, or ortho-xylene.

16. The method of claim 8 where the feedstock has a dry solids content between about 1 and 10 percent.